(12) United States Patent
Weichselbaum et al.

(10) Patent No.: US 7,961,311 B2
(45) Date of Patent: Jun. 14, 2011

(54) DETECTING AND COUNTING BACTERIA SUSPENDED IN BIOLOGICAL FLUIDS

(76) Inventors: Amnon Weichselbaum, Haifa (IL);
Jaime De La Zerda, Haifa (IL);
Issakhar Regev, Kibutz Eilon (IL)

( * ) Notice: Subject to any disclaimer, the term of this patent is extended or adjusted under 35 U.S.C. 154(b) by 0 days.

(21) Appl. No.: 12/810,838

(22) PCT Filed: Dec. 24, 2008

(86) PCT No.: PCT/IL2008/001663
§ 371 (c)(1),
(2), (4) Date: Jun. 26, 2010

(87) PCT Pub. No.: WO2009/083963
PCT Pub. Date: Jul. 9, 2009

(65) Prior Publication Data
US 2010/0277734 A1 Nov. 4, 2010

Related U.S. Application Data

(63) Continuation-in-part of application No. 11/573,788, filed as application No. PCT/IL2005/000884 on Aug. 16, 2005, now abandoned.

(60) Provisional application No. 60/601,644, filed on Aug. 16, 2004.

(51) Int. Cl.
*G01N 21/01* (2006.01)

(52) U.S. Cl. .......................................... 356/246; 356/341
(58) Field of Classification Search ............... 356/39–42, 356/337–341, 432, 436, 244, 246; 250/222.2; 422/82.05
See application file for complete search history.

(56) References Cited

U.S. PATENT DOCUMENTS

| 3,928,140 | A  | * | 12/1975 | Wyatt et al. | ..................... 435/32 |
| 6,230,045 | B1 | * | 5/2001 | Hoogenraad et al. | ......... 600/473 |
| 6,333,008 | B1 | * | 12/2001 | Leistner et al. | ................. 422/64 |
| 2004/0185552 | A1 | * | 9/2004 | Griner et al. | ............... 435/288.7 |
| 2006/0109476 | A1 | * | 5/2006 | Werner et al. | ................. 356/477 |
| 2006/0256338 | A1 | * | 11/2006 | Gratton et al. | ................ 356/417 |
| 2007/0159619 | A1 | * | 7/2007 | Chu et al. | ........................ 356/73 |

* cited by examiner

*Primary Examiner* — Tarifur Chowdhury
*Assistant Examiner* — Michael LaPage

(57) ABSTRACT

System and method for detecting and counting bacteria suspended in a biological fluid by means of light scattering measurements is provided. In accordance with the method of the invention the level of signal to noise of the measured intensities of light scattered by a sample of the biological fluid is significantly enhanced for forwardly scattered light within a range of scattering angles which are smaller compared to a predefined maximal scattering angle. The system of the invention includes a cuvette adapted to contain a sample of the biological fluid whose sidewalls and windows are suitably constructed and arranged to significantly reduce the level of reflected light obscuring the scattering patterns measured within the range of scattering angles considered.

17 Claims, 5 Drawing Sheets

DETECTING AND COUNTING BACTERIA SUSPENDED IN BIOLOGICAL FLUIDS

REFERENCE TO PREVIOUS APPLICATIONS

The present application is a continuation-in-part of U.S. patent application Ser. No. 11/573,788, filed on Feb. 16, 2007 now abandoned, which is a .sctn. 371 filing of international patent application Ser. No. PCT/IL05/000884, filed on Aug. 16, 2005, claiming the benefit of priority from US application for provisional patent Ser. No. 60/601,664, filed on Aug. 16, 2004.

FIELD OF THE INVENTION

The present invention relates in general to assaying a body fluid. In particular the present invention relates to optically testing urine, for the presence of bacteria at relatively low bacterial concentrations and to light scattering measurements.

BACKGROUND OF THE INVENTION

Detecting and counting bacteria suspended in a biological fluid by means of light scattering measurements is known. In US patent application 20070211251A1, which is incorporated herein by reference, a system and method for detecting and measuring the concentration of bacteria suspended in biological fluids, such as urine, by means of light scattering measurements are disclosed. The disclosed system includes cuvettes whose windows have any of the following feature: their refractive index is homogeneous, such that deviations of its values do not exceed $10^{-4}$, the root mean square of the changes in the surface roughness of the windows do not exceed 1 nanometer, the scratch/dig number associated with the surfaces of the windows does not exceed 40/20, and/or the widths of the windows do not exceed 500 micrometer (μm). The disclosed cuvettes are adapted to contain a sample of the biological fluid to be tested for the presence of bacteria by means of collimated light beam. The intensity of the scattered light is associated with a scattering profile to which is further compared to standard scattering profiles serving as a calibration scale. A set of standard scattering profiles comprises scattering profiles and linear combination of scattering profiles which were measured for suitable numbers of bacterial suspensions whose concentrations are known and further ensemble averaged.

Light scattering measurements are prone to errors at low concentrations of scatterers, such as of $10^4$ colony forming units per milliliter (CFU/ml) or lower levels. Therefore any system and method providing for relatively high sensitivity and specificity especially considering such low concentrations are beneficial.

SUMMARY OF THE PRESENT INVENTION

It is an object of the present invention to provide a method for detecting and measuring the concentration of bacteria suspended in a biological fluid, such as urine, by means of light scattering measurements. Such detecting and measuring are accomplished by considering forward scattering at scattering angles which are lower compared to a predefined maximal scattering angle, and suspensions having relatively low bacterial concentration of $10^4$ colony forming units per milliliter (CFU/ml) and/or lower. One bacterium is regarded hereinafter as one CFU.

It is another object of the present invention to provide a system for detecting and measuring the concentration of bacteria suspended in a biological fluid.

In accordance with the present invention there is provided a method for detecting bacteria suspended in a biological fluid by spatially filtering the light beam for illuminating the tested fluid, such that the level of the residual illuminating light received at a detecting segment disposed across the surface of the light detector is significantly decreased. Furthermore, in accordance with the present invention there is provided a method for reducing the level of light reflected towards the detecting segment disposed across the surface of the light detector by which the intensity of light scattered by the tested fluid is measured. Such reduction is accomplished by inclining the windows and skewing the sidewall, or sidewalls, of a cuvette adapted to contain a sample of the tested fluid.

Additionally in accordance with a preferred embodiment of the present invention there is provided a method for substantially canceling out components of the measured speckle images which are stationary in time thereby enhancing the signal to noise and/or signal to clatter ratios of the measured intensities of light scattered by the tested fluid. Scatterers, such as bacteria, which are moving at least in a Brownian motion, induce scattering patterns which are time dependent. Therefore, by successively mapping the instantaneous intensities of light received by the light detector within a predefined exposure time to generate pairs of speckle images; and by respectively subtracting one speckle image of a pair from the other, to form difference plots, most of the features related to the dynamics of the suspended bacteria are retained, whereas the features related to stationary background signals are substantially canceled out.

In accordance with the present invention there is provided a system for detecting, and measuring the concentration of, bacteria suspended in a biological fluid. The system of the invention has a spatial filter including two apertures the lengths of their respective diameters are predefined. The apertures are spaced apart by a predefined distance. The system of the invention further has a cuvette the sidewall or sidewalls of which are skewed. The windows of the cuvette are inclined by respective predefined tilting angles relative to the normal of the axis of the collimated beam. The system of the invention further comprises a light obscuring means for shading the face of an integral light detector. Additionally the system has a detecting segment associated with a predefined maximal scattering angle, for receiving scattered light its intensity is to be measured.

DETAILED DESCRIPTION OF THE PRESENT INVENTION

In accordance with the present invention a system and method for detecting and counting bacteria suspended in a biological fluid by means of light scattering measurements is provided. The system of the invention provides a collimated light beam for illuminating a sample of biological fluid to be tested for the presence of bacteria and for measuring the bacterial concentration. The illuminating beam is such structured and arranged according to the present invention that by means of a light obscuring means, which is integral to the system of the invention, the level of residual illuminating light impinging on the active surface of an integral light detector is significantly decreased. A sample of filtered fluid to exclude particles larger than the bacteria is filled into a cuvette. A cuvette of the invention has skewed sidewall or sidewalls and inclined windows, such structured and arranged to significantly decrease the level of reflected light that might interfere with the scattered light its intensity is to be measured. Measured intensities of the scattered light are associated with scattering profiles which are compared to a calibration scale. In accordance with a preferred embodiment of the present invention successively measured speckle images, which are instantaneous mappings of the intensities of scattered light measured within a predefined range of scattering angles, are subtracted to generate difference plots. The difference plots are further associated with scattering profiles to be compared to a respective calibration scale, as further described infra. The biological fluids considered, the measurement process and the preparation of calibration scales are further described in details in the referenced US patent application US20070211251A1. The system and method of the present invention are especially suited for assaying biological fluids having relatively, low bacterial concentrations, such as of 10,000 ($10^4$) CFU/ml and/or below.

Figure 1:
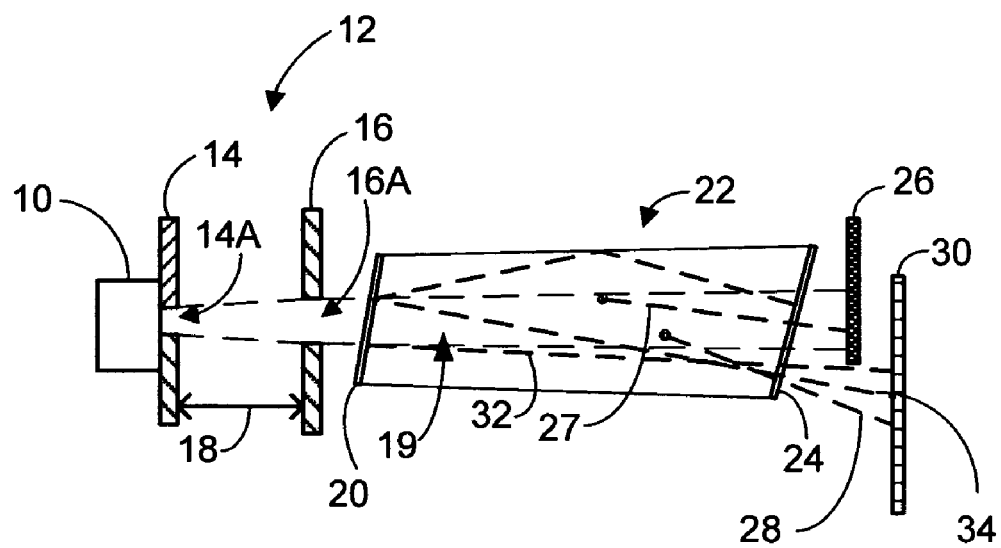
FIG. 1 is a scheme of a system for measuring the intensity of light scattered from a suspension contained in a cuvette in accordance with the present invention.
Figure 2:
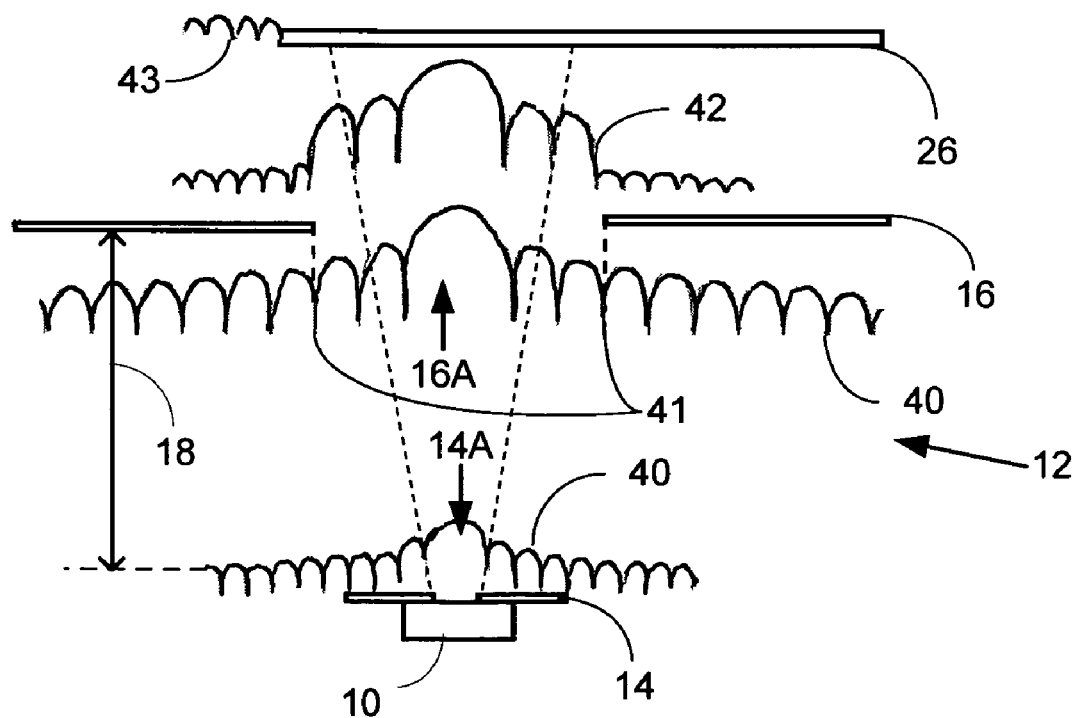
FIG. 2 is a schematic presentation of features of the illuminating beam according to a preferred embodiment of the present invention.

Reference is first made to FIGS. 1-2. In FIG. 1 a scheme of a system Do providing for measuring the intensity of light scattered from a sample of fluid in accordance with the method of the present invention is shown. In FIG. 2, features of the spatial filter providing for collimating the illuminating light beam and the light obscuring means, which are in accordance with a preferred embodiment of the present invention, are schematically shown. (Same parts are indicated in FIGS. 1-2 by the same numbers.) Light emitted from light source 10 propagates through spatial filter 12 having two diaphragms 14 and 16, on which apertures 14A and 16A are coaxially disposed respectively. In accordance with the method of the present invention the diaphragms are separated by a predefined distance designated by double arrow 18. Furthermore, the respective magnitudes of the diameters of apertures 14A and 16A are predefined. Exemplary light source according to the invention is a laser having a predefined wavelength. Illuminating light beam 19 emerges off the spatial filter 12 and penetrates window 20 to illuminate a portion of the fluid contained within cuvette 22 along its way through window 24 towards the light detector. Most of illuminating beam 19 is blocked by light obscuring means 26 and therefore cannot reach the light detector. Some of the forwardly scattered light, such as ray 27, is blocked by light obscuring means 26 as well. A portion of the scattered light, such as ray 28, impinges on the surface of light detector 30. The signal received at a specific point disposed at the surface of detector 30 is considered as the intensity of light scattered at a given scattering angle, as known. Some of the illuminating light, such as ray 32, which is scattered from a surface of window 20, or illuminating ray 34, which is reflected by window 22 and again by window 20, may get to the active surface of detector 30 and interfere with the scattered light, thereby obscuring its level.

Diminishing Interferences Caused by Residual Illuminating

Spatially filtering and/or collimating of the illuminating light beam according to the present invention, such as by means of spatial filter 12, provides for significantly decreasing the level of the residual illuminating beam faced by the light detector. The diameter of aperture 14A is selected by considering the radius and/or the cone angle of the illuminating beam, as known. This aperture provides for a well defined diffraction pattern symbolically presented by pattern 40 which represents the Bessel function of the first kind associated with the beam emerging off aperture 14A. Typically the diameter of aperture 14A ranges from 50 to 500 microns. The lower limit of such diameter is derived in consideration with the detection limit of the light detector employed. Smaller diameters cannot provide the desired level of illumination namely, the level of the scattered light impinging on the light detector is too low to be detected. On the other hand, apertures that are too large produce side lobes having intensities and spatial features that make them practically difficult to be screened out. The level of the residual illuminating light faced by the light detector is determined in accordance with a preferred embodiment of the present invention by selecting the radius of aperture 16A to comply with a zero of the Bessel function of the first kind associated with the angular profile, such as pattern 40, of the beam emerging off aperture 14A. The radius of aperture 16A is determined by the angle corresponding to the selected zero 41 and the magnitude of the distance 18 separating between diaphragms 14 and 16. The angular profile of the beam emerging off aperture 16A symbolically presented by pattern 42, has side-lobes the levels of which are substantially lower compared to the level of the side-lobes of pattern 40. Theoretically, by extending distance 18 and by employing sharp apertures one can significantly reduce the level of the side-lobes of pattern 42. However such target is difficult to practically achieve. Therefore in accordance with the method of the present invention a light obscuring means, such as light obscuring means 26, is disposed such that it totally blocks most of this beam. The edge of light obscuring means 26, which determines a rim of the detecting segment, which is the region across the active face of the light detector in which the intensity of the scattered light is measured, produces additional diffraction pattern across the face of the detector, designated by pattern 43.

Diminishing Interferences Caused by Reflected Light

Figure 3:
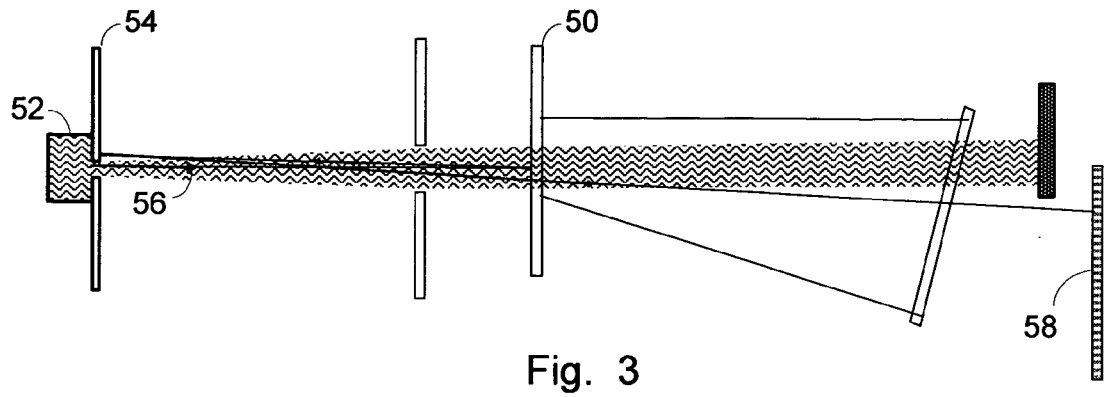
FIG. 3 is a scheme of a system for measuring the intensity of light scattered from a fluid contained in a cuvette considering light reflected from a window of the cuvette.
Figure 4:
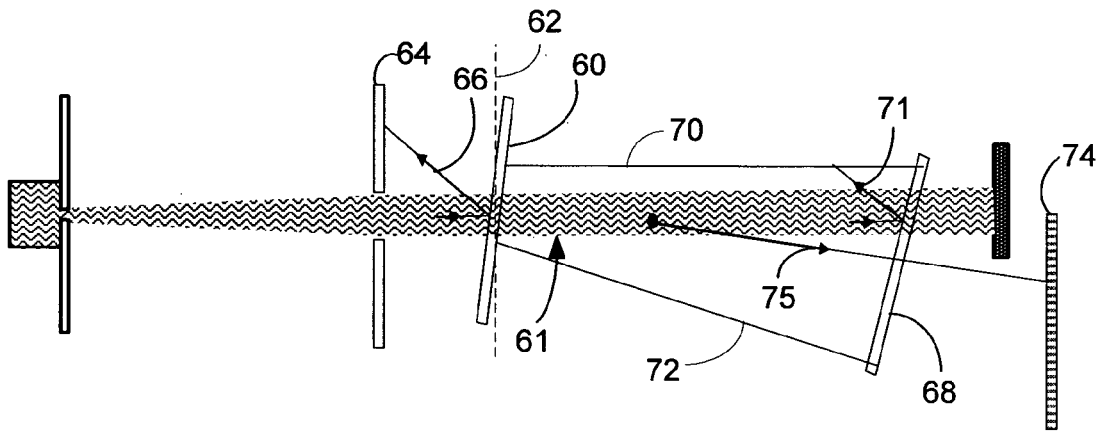
FIG. 4 is a scheme of the system shown in FIG. 3 in which a cuvette in accordance with the present invention is incorporated.

The windows of the cuvettes employed in accordance with the present invention are such constructed and arranged to decrease the level of the reflected light faced by the light detector. Reference is now made to FIGS. 3-4. In a case in which a window of a cuvette, such as window 50, is perpendicular to the axis of the illuminating beam, as shown in FIG. 3, multiple reflections occurring between the window and the face of light source 52 and/or diaphragm 54, such as ray 56, may result in a signal detected by light detector 58. Therefore the window adjacent to the light source is inclined relative to the beam normal by a predefined tilting angle as is shown in FIG. 4. Window 60 is shown clockwise tilted by a predefined angle relative to beam normal 62. Typical tilting angles in accordance with the present invention are in the range of 2°-15°. Preferable are tilting angles not exceeding 10°. Most of the light reflected by window 60 in such cases is directed such that it cannot be detected by the light detector, similarly to ray 66 that cannot be reflected back into the cuvette and further propagate towards the light detector. Window 68, which is adjacent to the light detector, is further tilted in the same direction in which window 60 is tilted. Since the reflectance of the sidewall is significantly increased as the angle of incidence approaches 90°, the angle by which window 68 is further rotated relative to window 60 need not be too large, as the angle of incidence of a reflected ray with sidewall 70, such as ray 71, respectively increases by such rotations. In accordance with a preferred embodiment of the present invention the second window is inclined in the same direction by a tilting angle which is larger by about 8° compared to the tilting angle of window 60.

Furthermore, opposing surfaces of the sidewall or sidewalls of the cuvette, such as walls 70 and 72 are not parallel, but are mutually inclined, such that their tangential plans intersect each other at the side of the cuvette where the light source is disposed. The geometrical shape of a cuvette in accordance with a preferred embodiment of the present invention is of a truncated cone. The windows of such cuvette respectively constitute the small and large bases of the truncated cone. The windows are respectively tilted relative to the cone's axis towards the same direction by tilting angles as described above. The conical cuvettes are placed within the system such that their large bases are adjacent to the light detector. Such or similarly inclined sidewall or sidewalls, are individually or collectively referred hereinafter as skewed sidewall. Light reflected by such skewed sidewall normally diverges and therefore hardly reach a predefined segment of the active face of the light detector. Namely, the chances for multiple reflections induced by a skewed sidewall and/or windows such inclined, to impinge on a predefined segment of the surface of light detector 74 are significantly decreased. Therefore such decreasing of the level of reflected light as described above, provides for improving the signal to noise ratio of the system of the invention and for enhancing its sensitivity. Further coating the respective surfaces of the windows, sidewalls, and of the diaphragms of a spatial filter with suitable anti-reflecting and/or absorbing layers, as known, is in accordance with the present invention.

Maximal Scattering Angle

Figure 5:
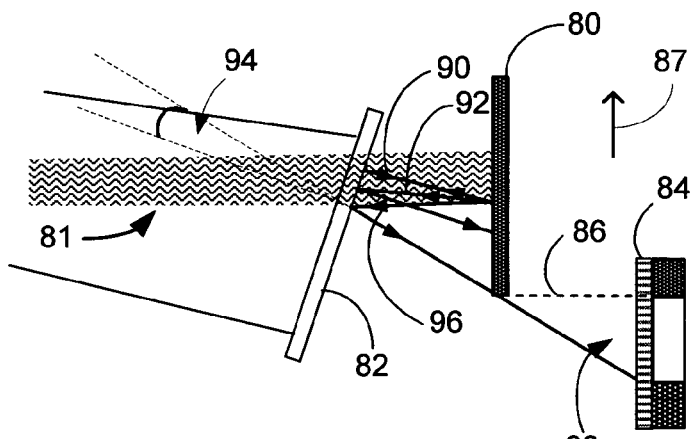
FIG. 5 schematically describes a segment of the system shown in FIG. 4.

Reference is now made to FIG. 5 in which a segment of a system for detecting and counting bacteria according to an embodiment of the present invention is schematically shown. Light obscuring means 80 illuminated by light beam 81 is such disposed according to the present invention that it blocks most of the illuminating beam on its way towards the surface of the light detector. Embodiment variants in which the light obscuring means is placed within the cuvette, and/or attached to any of the surfaces of the window adjacent to the light detector, and/or positioned behind the said window, are in accordance with the present invention. For the sake of simple explanation an exemplary configuration of the system is hereby described in which light obscuring means 80 is disposed between window 82 and light detector 84. Light obscuring means shades the surface of light detector 84, such that a fully shaded region is disposed above dashed line 86 in the plane of FIG. 5 (in the same direction in which arrow 87 points). Detecting segment 88, which is the segment of the active surface of the light detector providing for measuring the intensity of scattered light in accordance with the present invention, is disposed below dashed line 86 (in the opposite direction to which arrow 87 points). The lower end of this range of scattering angles is limited by the projection of the respective segment of the edge of light obscuring means across the detector's face, which is the rim of the fully shadowed region across the surface of light detector 84. The other end at a given azimuthal angle (in consideration with a coordinate system whose z axis coincides with the axis of the illuminating beam) is predefined in accordance with the method of the present invention. Exemplary reflected light ray 90 emerges off light obscuring means from a point circumferential to the illuminated area across the face of light obscuring means 80. Ray 90 perpendicularly impinges on the surface of window 82 (at a zero angle of incidence). Therefore this ray 90, is reflected back to propagate along the line coinciding with the track of the original ray 90. Another exemplary reflected ray 92 whose angle of incidence with window 82 is larger compared to the angle of incidence of ray 90 is reflected back to impinge on light obscuring means 80. Only rays reflected at angles that are not smaller than angle 94 can be reflected from window 82 to impinge on the surface of detector 84 at points external to detecting segment 88. Therefore limiting the scattering angle in which the intensity of scattered light is measured to an upper threshold, which is the maximal scattering angle according to the present invention, the value of which closely equals the magnitude of angle 94, provides for lowering the level of reflected light and diminishing the level of noise obscuring the level of scattered light.

Experiments concerning the sensitivity of a system for detecting and counting bacteria according to a preferred embodiment of the present invention are described in the examples below with reference to FIGS. 6-10. The system considered comprises: a laser; a collimator having two diaphragms separated accordingly whose respective apertures are of suitable diameters; a cuvette having tilted windows and a skewed sidewall, which is conically shaped; a circular light obscuring means placed between the cuvette and the light to detector, which is implemented by a monolithic two dimensional detector array, and a processor for controlling the measurements process and carrying out the computational tasks involved, as further described infra and detailed in US patent application US20070211251A1, incorporated herein by reference.

EXAMPLE 1

Figure 6:
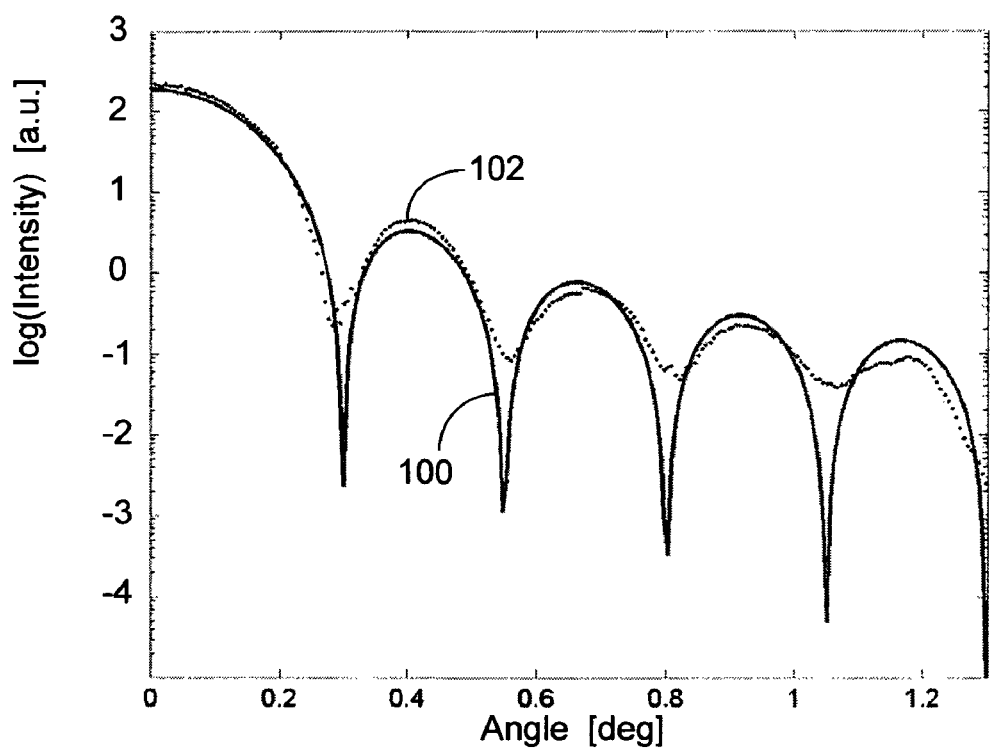
FIG. 6 is a graph comparing between computed and measured angular beam profiles corresponding to an exemplary aperture.
Figure 7:
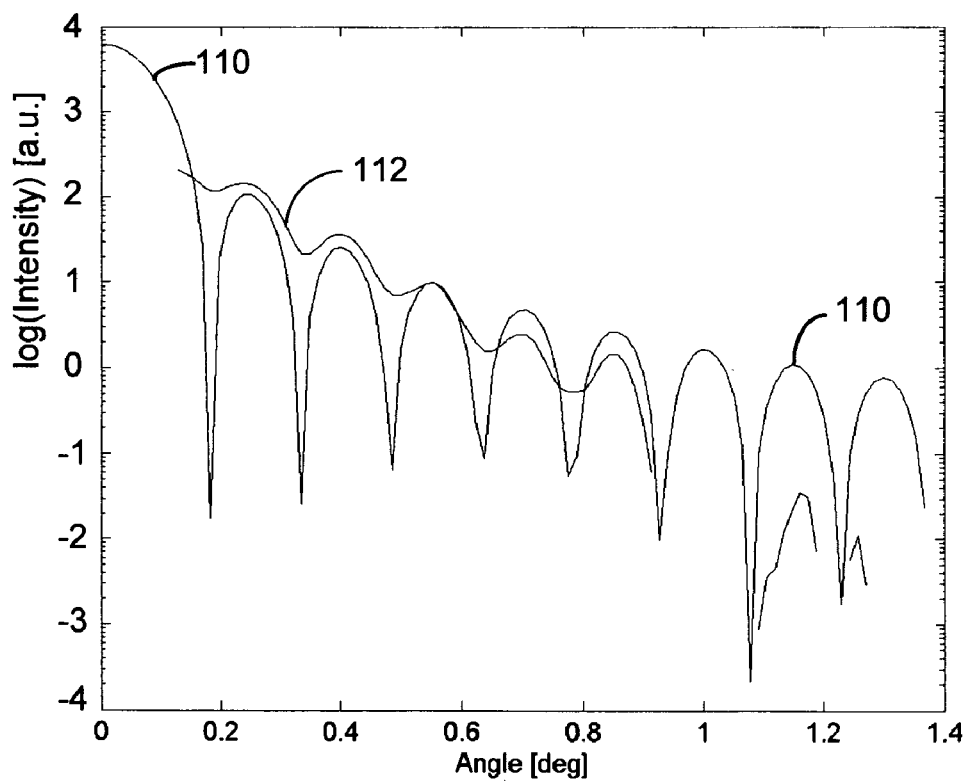
FIG. 7 is a graph comparing between measured and computed angular beam profiles corresponding to another aperture different than the aperture considered in FIG. 6.

In FIGS. 6 and 7 graphs comparing between calculated and measured angular beam profiles generated by means of apertures having different diameters are respectively shown. Plots 100 and 102 respectively correspond to the calculated and measured profiles when employing aperture having a diameter of 150 μm. Similarly plots 110 and 112 respectively correspond to calculated and measured intensities when employing aperture of 500 μm. The intensity of light at a diffraction angle $\theta I(\theta)$, is given according to diffraction theory by equation (1):

$$I(\theta) = \left(\frac{J_1(ka\theta)}{ka\theta}\right)^2, \quad (1)$$

where $J_1$—is the Bessel function of the first kind, a—is the aperture radius, and k—is the wave-number. The calculated and measured intensities shown in a logarithmic scale are measured in arbitrary units (A.U.); the angles are measured in degrees.

The width of a beam emerging off an aperture of radius a–w(a), is given by equation (2):

$$\omega = 2a + \frac{2}{\pi}\frac{\lambda}{a}L, \quad (2)$$

where $\lambda$—is the wavelength, a—is the radius and L—designates the distance along which the beam has propagated.

Figure 8:
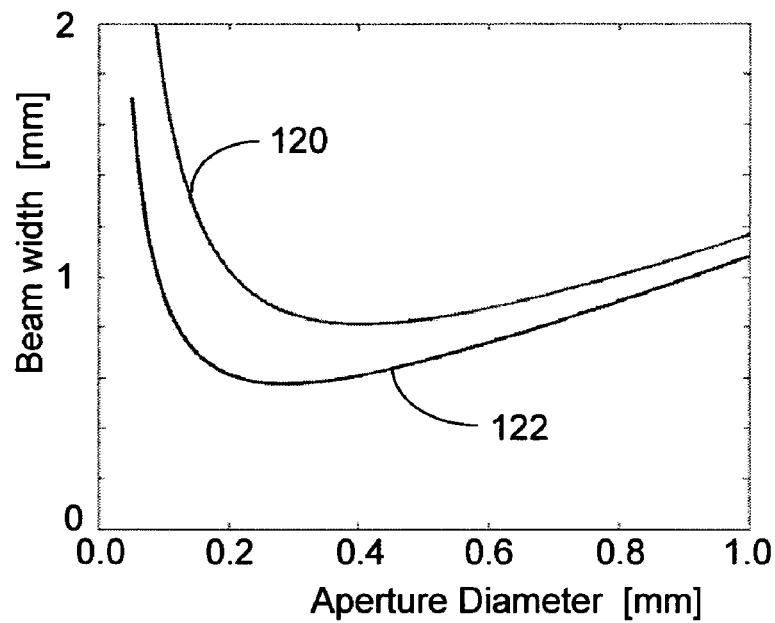
FIG. 8 is a graph of beam-widths as a function of the diameter of the aperture computed for two exemplary points respectively disposed at 100 mm and 200 mm away off the aperture.

In FIG. 8 a graph comparing between beam widths respectively calculated for L=100 millimeters (mm)—plot 120 and L=200 mm—plot 122 are shown as a function of the diameter of the aperture generating the beam. The widths of the beams and the diameters are measured in millimeters (mm). As the illuminated volume containing the scatterers is dependent on the value of the beam-width, it is desired to select for the second aperture disposed closer to the cuvette the maximal diameter in consideration with the zeros of the Bessel function associated with the first aperture, which is adjacent to the laser. Respectively selecting diameters of 300 microns (μm) and 500 μm for the second aperture, which is adjacent to the cuvette, results in a beam having a width of about 0.6 mm. Naturally, larger apertures are preferable as they are capable for transmitting higher illuminating intensities. Therefore it is preferable according to the present invention to select a zero of the Bessel function of the first aperture which corresponds to a point disposed on the respective plot above its minimum. The level of the side-lobes of the beam emerging off the second aperture decreases as the separation L increases (due to better spatial separation between adjacent zeros), therefore L=200 mm in this example is preferable to L=100 mm.

EXAMPLE 2

Figure 9:
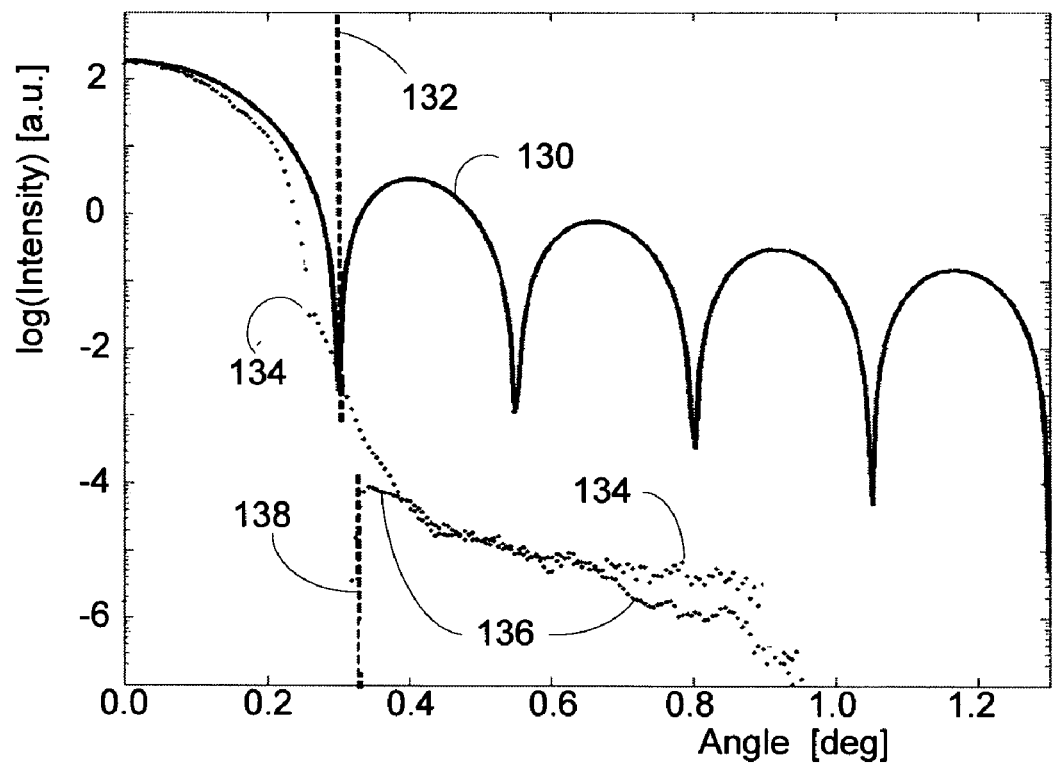
FIG. 9 is a graph comparing among angular profiles of three different beams computed or measured across the face of the light detector.

In FIG. 9 a graph comparing between the intensities of the residual illuminating light received at the detector as a function of the scattering angle, with and without the light obscuring means disposed in its place is respectively shown. The intensities shown are measured in arbitrary units (A.U.) employing logarithmic scale. Plot 130 presents the computed beam profile considering the first aperture, which is adjacent to the laser. Dashed line 132 presents the scattering angle corresponding to the diameter of the second apertures which complies with the first zero of the respective Bessel function. Plot 134 presents the intensity of the illuminating beam emerging off the second aperture as a function of the scattering angle when the light obscuring means is avoided. Plot 136 presents the intensity of the residual illuminating light received by the light detector when the light obscuring means is positioned in its place. Dashed line 138 presents the scattering angle corresponding to the edge of the light obscuring means. In cases in which the dynamic range of the light detector namely, its sensitivity provides for measuring intensities within a range of $10^{-7}$–1, the system incorporating a light obscuring means provide for measuring the desired scattering profiles within a range of angles staring around 0.8° up to the angle corresponding to the detection limit of the detector.

EXAMPLE 3

Figure 10:
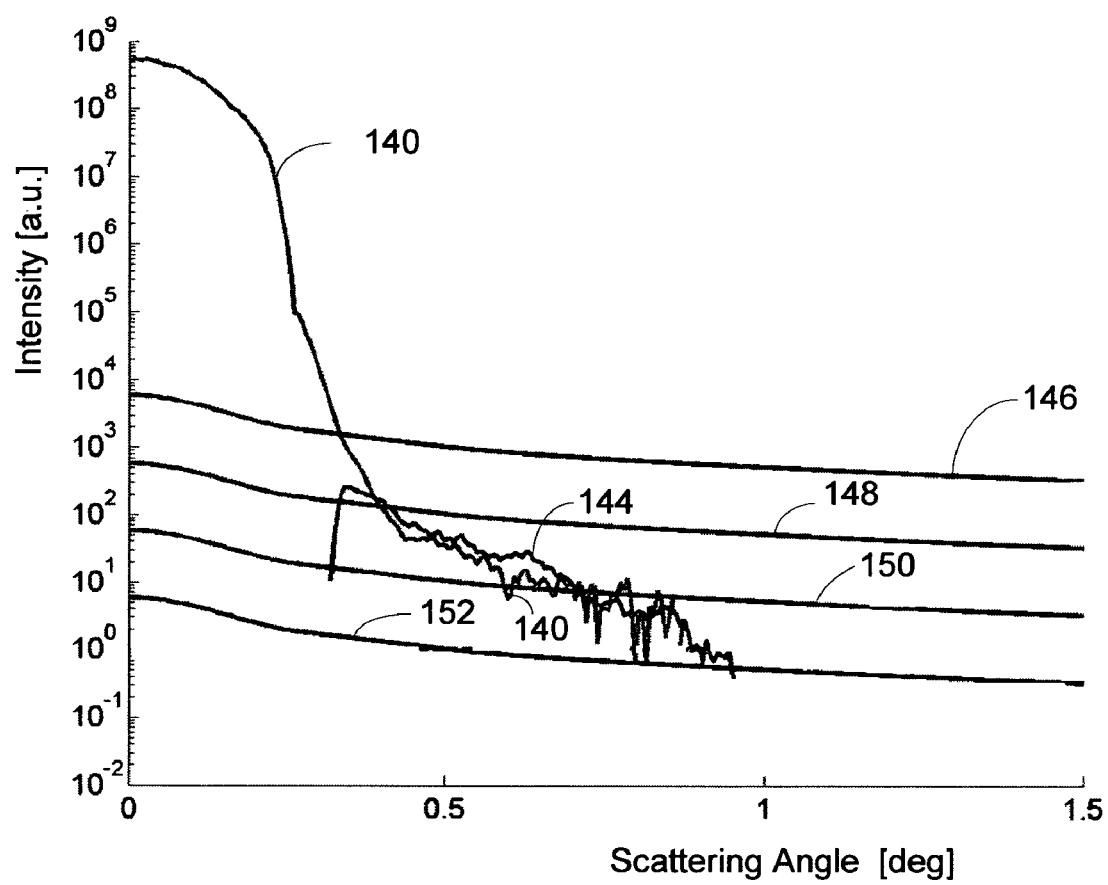
FIG. 10 is a graph comparing among the intensity of light received at the light detector considering two different beams and computed scattering profiles considering various concentrations of scatterers.

In FIG. 10 a graph comparing among the intensities of the residual illuminating light received at the detector and exemplary scattering profiles computed for various bacterial concentrations is shown. Plot 140 presents the intensity of light received at the light detector as a function of the scattering angle when the light obscuring means is avoided. Plot 144 presents the angular profile of the residual illumination when the light obscuring means is positioned in place. Plots 146, 148, 150, 152 present scattering profiles computed according to the Mie theory for bacterial concentrations of $10^6$, $10^5$, $10^4$, $10^3$ respectively. The bacterial model employed consists of spheres evenly suspended in a liquid, having radii of 1.5 μm whose refracting index equals 1.35, whereas the refracting index of the liquid equals 1.33. For practical purposes and by considering the dynamic ranges of detectors available in the marketplace the maximal scattering angle need not according to the present invention exceed 2° and preferably be equal or lower than 1.5°. In a case in which a detector whose dynamic range is higher is available, the maximal scattering angle can be extended up to the value similarly derived from the respective detection limit.

Detecting and Counting Bacteria Suspended in a Biological Fluid.

The signals induced along a predefined exposure time by the light impinging across the detecting segment of the light detector provide for generating a speckle image. Such speckle images vary in time due to at least the Brownian motion of the scatterers. However the components of these speckle images, such as signals induced by residual illuminating light, multiple reflections and or impurities of the illuminating beam, impurities or defects located on the surfaces of, or embedded within, the cuvettes' windows, are stationary in time. Therefore by subtracting successively measured speckle images the stationary components are substantially canceled out, whereas the time dependent components such as of the scattering patterns induced by the moving scatterers are retained. In turn the sensitivity of the system of the invention in measuring relatively low bacterial concentrations is significantly enhanced.

In accordance with a preferred embodiment of the present invention first the signals received across the detecting segment of the light detector within predefined exposure times, such as of 10 milliseconds (ms), is repeatedly sampled at predefined repetition rates, such as 100 Hertz (Hz), to generate successively measured speckle images. Then pairs of successively measured speckle images are selected and one speckle image of a selected pair is subtracted from the other speckle image of this pair to form a respective difference plot by considering the absolute values of the respective differences. Optionally a number of difference plots are further averaged, as known, to generate averaged difference plots. Scattering profiles are associated with selected difference plots or with the averaged difference plots. The scattering profiles are further compared to a calibration scale which includes standard scattering profile selected from a set of pre-stored scattering profiles. A set of standard scattering profiles includes according to the present invention scattering profiles and linear combinations of scattering profiles similarly measured for suspensions having given bacterial concentrations. The exposure times and the repetition rates are selected according to the present invention in consideration with the velocity distribution associated with the Brownian motion at a given temperature. Too long exposure times may smear the difference plot due to the scatterers' motion. In addition, low repetition rates do not allow for differentiating between Brownian motion and the relatively faster motion of motile bacteria. Therefore at a given temperature a minimal repetition rate is selected considering the changes in the scattering angles that might occur due to the Brownian motion along the respective cycle times involved.

Alternatively, scattering profiles are associated with the measured intensities of the scattered light, such as by means of curve fitting as known. Optionally these scattering profiles are averaged in time and/or across a range of azimuthal angles, as known. These scattering profiles and/or respective averaged scattering profiles are further compared to calibration scale as detailed in the referenced patent application US20070211251A1.

The invention claimed is:

1. A method for detecting bacteria suspended in a biological fluid by means of a system for detecting bacteria having a light source for generating an illuminating light beam having an axis to illuminate a portion of said biological fluid and a light detector for receiving light forwardly scattered by said portion of biological fluid, wherein said portion of biological fluid contained in a cuvette axially disposed with said illuminating beam, and wherein said cuvette has a skewed sidewall and two windows, said method comprising:
   a. decreasing the level of direct illuminating light propagating towards said light detector;
   b. decreasing the level of light reflected off any of said sidewall and windows propagating towards a predefined segment disposed across a plane of said light detector;
   c. measuring the intensity of light scattered by said biological fluid at least at one scattering angle;
   d. comparing said measured intensities to a calibration scale, and
wherein said at least one scattering angle measured relative to said axis, and wherein said at least one scattering angle does not exceed a predefined maximal scattering angle and wherein said decreasing the level of light reflected off any of said sidewall and windows accomplished by inclining said sidewall and windows relative to the normal of said axis.

2. A method as in claim 1, wherein said maximal angle does not exceed 2 degrees.

3. A method as in claim 1, further comprising:
   a. measuring the intensity of light scattered by said biological fluid at a second scattering angle;
   b. associating a scattering profile with said measured intensities, and
wherein said second scattering angle is different from said at least one scattering angle and is not larger than said maximal scattering angle.

4. A method as in claim 3, further comprising matching to said associated scattering profile any item selected from a group of items consisting of pre-stored calibrated scattering profiles and linear combinations of pre-stored calibrated scattering profiles.

5. A method as in claim 1, further comprising:
   a. successively measuring at least twice said intensity of scattered light, wherein said measuring is accomplished at a rate not lower compared to a predefined minimal repetition rate, and
   b. associating a difference plot with said successively measured intensities, and
wherein said successively measuring is accomplished at the said at least one scattering angle, and wherein said minimal repetition rate compatible with the dynamics of said bacteria suspended in said biological fluid.

6. A method as in claim 5, further comprising:
   a. successively measuring at least twice the intensity of light scattered by said biological fluid at a second scattering angle, wherein said successively measuring is accomplished at the same said rate, and wherein said second scattering angle is different from said at least one scattering angle;
   b. associating difference plots with said successively measured intensities;
   c. associating scattering profile to said difference plots, and
   d. matching to said associated scattering profile any item selected from a group of items consisting of pre-stored calibrated scattering profiles and linear combinations of pre-stored calibrated scattering profiles.

7. A method as in claim 1, wherein the concentration of said bacteria in said biological fluid does not exceed $10^{-4}$ CFU/ml.

8. A method as in claim 1, wherein said decreasing the level of direct illuminating light effected by means of light obscuring means disposed between said light detector and said portion of biological fluid.

9. A method as in claim 1, further comprising decreasing the level of residual illuminating light propagating towards said light detector by collimating said illuminating light beam by means of a spatial filter disposed between said light source and said portion of biological fluid, wherein said spatial filter comprises:
   a first aperture in a diaphragm having a predefined diameter;
   a second aperture in a diaphragm spaced apart from said first aperture, and
wherein the diameter of said second aperture complies with a zero of the Bessel function of the first kind associated with a beam of light emerging off said first aperture.

10. A system for detecting bacteria suspended in a biological fluid having a light source for generating an illuminating light beam having an axis and a light detector, said system comprising a cuvette having two windows and skewed sidewall, said cuvette adapted to contain a sample of said biological fluid, wherein one of said windows, which is the first of said windows, is inclined relative to the normal of said axis by a first predefined angle, and wherein the second of said windows is inclined relative to the normal of said axis by a second predefined angle which is different from the first predefined angle, and wherein said first predefined angle and said second predefined angles correspond to rotations at the same direction.

11. A system as in claim 10, further comprising a spatial filter disposed adjacent to said light source, wherein said spatial filter comprises:
   a first aperture disposed adjacent to said light source, and
   a second aperture coaxial with the first aperture spaced apart from said first aperture by a predefined distance.

12. A system as in claim 11, wherein the diameter of said second aperture complies with a zero of the Bessel function of the first kind associated with a beam of light emerging off said first aperture.

13. A system as in claim 11, further comprising a light obscuring means for shading a segment across the face of said light detector.

14. A system as in claim 11, further comprising a detecting segment disposed across a surface of said light detector, wherein said detecting segment associated with a maximal scattering angle.

15. A system as in claim 10, wherein the magnitude of said first predefined angle is in the range of 1.5°-2°.

16. A system as in claim 15, wherein the second predefined angle is larger compared to the magnitude of said first predefined angle.

17. A system as in claim 16, wherein the magnitude of the second predefined angle is larger by 8° compared to the magnitude of said first predefined angle.

* * * * *